(12) United States Patent
Rouet et al.

(10) Patent No.: US 11,607,186 B2
(45) Date of Patent: *Mar. 21, 2023

(54) VISUALIZING VASCULAR STRUCTURES

(71) Applicant: KONINKLIJKE PHILIPS N.V., Eindhoven (NL)

(72) Inventors: Laurence Rouet, Paris (FR); Raoul Florent, Ville d'Avray (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 44 days.

This patent is subject to a terminal disclaimer.

(21) Appl. No.: 17/194,359

(22) Filed: Mar. 8, 2021

(65) Prior Publication Data
US 2021/0186444 A1 Jun. 24, 2021

Related U.S. Application Data (63) Continuation of application No. 16/469,396, filed as application No. PCT/EP2017/082895 on Dec. 14, 2017, now Pat. No. 10,939,885.

(30) Foreign Application Priority Data

Dec. 15, 2016 (EP) .................................. 16306688

(51) Int. Cl.
*A61B 6/00* (2006.01)
*G06T 5/00* (2006.01)
*G06T 5/50* (2006.01)

(52) U.S. Cl.
CPC ............ *A61B 6/463* (2013.01); *A61B 6/4441* (2013.01); *A61B 6/504* (2013.01); *A61B 6/5264* (2013.01);
(Continued)

(58) Field of Classification Search
CPC ........ A61B 6/463; A61B 6/4441; A61B 6/504; A61B 6/5264; A61B 6/481; A61B 6/12;
(Continued)

(56) References Cited

U.S. PATENT DOCUMENTS 5,848,121 A 12/1998 Gupta
5,852,646 A 12/1998 Klotz
(Continued)

FOREIGN PATENT DOCUMENTS

CN 101370430 A 2/2009
WO 2008129484 A2 10/2008
(Continued)

OTHER PUBLICATIONS

Hiroshima et al: "Digital Subtraction Angiogram Registration Method with Local Distortion Vectors to Decrease Motion Artifact"; Journal of Biomedical Informatics, 34, pp. 182-194 (2001).
(Continued)

*Primary Examiner* — Michael S Osinski (57) ABSTRACT

A system, device, and method for visualizing vascular structures is disclosed. According to some implementations, in order to provide further improved digital subtraction angiography, a device for visualizing vascular structures is provided that includes a data provision processor, an image processor, and an output. The data provision processor is configured to provide a first sequence of non-contrast X-ray images of a region of interest of a patient for use as raw X-ray mask images. The data provision processor is also configured to provide a second sequence of contrast X-ray images of the region of interest of a patient for use as raw X-ray live-images. The image processor is configured to perform a first spatial subtraction for the first sequence of non-contrast X-ray images resulting in a first sequence of spatial-subtracted mask images. The image processor is also
(Continued)

configured to perform a second spatial subtraction for the second sequence of contrast X-ray images resulting in a second sequence of spatial-subtracted X-ray live-images. The image processor is further configured to perform a temporal subtraction by subtracting the spatial-subtracted mask images from the spatial-subtracted X-ray live-images resulting in a sequence of spatial-temporal subtracted X-ray live-images. The output is configured to output the sequence of spatial-temporal subtracted X-ray live-images.

20 Claims, 4 Drawing Sheets

(52) U.S. Cl.
CPC ............... G06T 5/002 (2013.01); G06T 5/50 (2013.01); *G06T 2207/10116* (2013.01); *G06T 2207/20224* (2013.01)

(58) Field of Classification Search
CPC ..... A61B 6/5235; A61B 6/032; A61B 6/5217; A61B 6/482; A61B 6/486; A61B 6/469; A61B 6/487; A61B 6/5211; A61B 6/5258; A61B 6/0407; A61B 6/461; A61B 6/484; A61B 6/5205; A61B 6/5241; G06T 5/002; G06T 5/50; G06T 2207/10116; G06T 2207/20224; G06T 2207/30101; G06T 2207/10081; G06T 7/0012; G06T 2207/30104; G06T 7/0016; G06T 11/008
See application file for complete search history.

(56) References Cited

U.S. PATENT DOCUMENTS

| | | |
|---|---|---|
| 7,545,967 B1 | 6/2009 | Prince |
| 7,826,884 B2 | 11/2010 | Baumgart |
| 8,643,642 B2 | 2/2014 | Mistretta |
| 10,217,247 B2 | 2/2019 | Carmi |
| 10,628,940 B2 | 4/2020 | Srivastava |
| 10,755,455 B1 | 8/2020 | Kaethner |
| 10,813,609 B2 | 10/2020 | Goto |
| 2002/0041654 A1 | 4/2002 | Hayashi |
| 2003/0031299 A1 | 2/2003 | Ohishi |
| 2006/0023840 A1 | 2/2006 | Boese |
| 2007/0195932 A1 | 8/2007 | Nakaura |
| 2008/0027316 A1 | 1/2008 | Baumgart |
| 2008/0037844 A1 | 12/2008 | Baumbart |
| 2009/0010380 A1 | 1/2009 | Gotoh |
| 2010/0034446 A1 | 2/2010 | Zhu |
| 2010/0172474 A1 | 7/2010 | Vogt |
| 2010/0202675 A1 | 8/2010 | Takanaka |
| 2010/0208973 A1 | 8/2010 | Lienard |
| 2011/0235889 A1 | 9/2011 | Spahn |
| 2011/0293162 A1 | 12/2011 | Pajeau |
| 2012/0207270 A1 | 8/2012 | Flohr |
| 2012/0238871 A1 | 9/2012 | Pfister |
| 2012/0243759 A1 | 9/2012 | Fujisawa |
| 2013/0216119 A1 | 8/2013 | Baumgard |
| 2014/0270437 A1 | 9/2014 | Shreiber |
| 2015/0071520 A1 | 3/2015 | Takemoto |
| 2015/0139514 A1 | 5/2015 | Mohr |
| 2015/0150526 A1 | 6/2015 | Ohishi |
| 2015/0346303 A1 | 12/2015 | Hu |
| 2016/0015348 A1 | 1/2016 | Ohishi |
| 2016/0022236 A1 | 1/2016 | Ohishi |
| 2016/0180525 A1 | 6/2016 | Reynolds |
| 2016/0206271 A1 | 7/2016 | Han |
| 2016/0350913 A1 | 12/2016 | Nagae |
| 2016/0371862 A1 | 12/2016 | Silver |
| 2017/0103526 A1 | 4/2017 | Zaiki |
| 2017/0228857 A1 | 8/2017 | Carmi |
| 2017/0345145 A1 | 11/2017 | Nempont |
| 2017/0347982 A1 | 12/2017 | Rouet |
| 2018/0235563 A1 | 8/2018 | Nam |
| 2018/0368793 A1 | 12/2018 | Ohishi |
| 2019/0269329 A1 | 9/2019 | Franjic |
| 2019/0274651 A1 | 9/2019 | Ohasi |
| 2020/0069276 A1 | 3/2020 | Yosida |
| 2020/0074700 A1 | 3/2020 | Kowarschik |
| 2020/0330063 A1 | 10/2020 | Thibault Pelletier |

FOREIGN PATENT DOCUMENTS

| | | |
|---|---|---|
| WO | 2016083068 A1 | 6/2016 |
| WO | 2016110420 A1 | 7/2016 |

OTHER PUBLICATIONS

Meijering et al: "Retrospective Motion Correction in Digital Subtraction Angiography" A Review; IEEE Transactions on Medical Imaging, vol. 18, No. 1, Jan. 1999.
PCT/EP2017/082895 ISR and Written Opinion, dated Apr. 26, 2018, 14 Pages.

VISUALIZING VASCULAR STRUCTURES

CROSS-REFERENCE TO RELATED APPLICATIONS

This application is a continuation of U.S. application Ser. No. 16/469,396 filed on Jun. 13, 2019, which is a U.S. National Phase application under 35 U.S.C. § 371 of International Application No. PCT/EP2017/082895, filed on Dec. 14, 2017, which claims the benefit of European Patent Application No. 16306688.9, filed on Dec. 15, 2016. These applications are hereby incorporated by reference herein in their entirety.

FIELD

The present invention relates to visualizing vascular structures, and relates in particular to a device for visualizing vascular structures, to a medical imaging system and to a method for visualizing vascular structures.

BACKGROUND

In interventional X-ray imaging, digital subtraction angiography (DSA) may be performed to visualize vascular structures. To emphasize the vascular structures, contrast agent is injected. Images may be obtained by subtracting a non-injected mask frame from injected frames. In case of motion, and in particular breathing or bowel gas motion, the quality of subtracted images may be affected and the resulting artifacts may influence the diagnostic value of the images. To reduce this effect, as an example, the motion vector field between mask and current frame is detected. The mask is then warped in order to be better aligned with the current frame before subtraction is performed.

For an improved result, WO2016110420 describes digital subtraction angiography with a double-temporal subtraction for artifacts reduction. Also, WO2016083068 describes digital subtraction angiography with separate compensation for breathing and cardiac motion artifacts.

SUMMARY OF THE INVENTION

There may be a need to provide further improved digital subtraction angiography.

The object of the present invention is solved by the subject-matter of the independent claims; further embodiments are incorporated in the dependent claims. It should be noted that the following described aspects of the invention apply also for the device for visualizing vascular structures, for the medical imaging system and for the method for visualizing vascular structures.

According to an aspect, a device for visualizing vascular structures is provided. The device comprises a data provision processor, a data image processor, and an output interface. The data provision processor is configured to provide a first sequence of non-contrast X-ray images of a region of interest of a patient for use as raw X-ray mask images. The data provision processor is also configured to provide a second sequence of contrast X-ray images of the region of interest of a patient for use as raw X-ray live-images. The image processor is configured to perform a first spatial subtraction for the first sequence of non-contrast X-ray images resulting in a first sequence of spatial-subtracted mask images. The image processor is also configured to perform a second spatial subtraction for the second sequence of contrast X-ray images resulting in a second sequence of spatial-subtracted X-ray live-images. The image processor is further configured to perform a temporal subtraction by subtracting the spatial-subtracted mask images from the spatial-subtracted X-ray live-images resulting in a sequence of spatial-temporal subtracted X-ray live-images. The output interface is configured to output the sequence of spatial-temporal subtracted X-ray live-images.

Since X-ray images are transparency images and observed motion may result from the super-imposition of various motion layers with different characteristics, the spatial subtraction supports in compensating for sources of motion.

According to an example, a display is provided, which is configured to display the sequence of spatial-temporal subtracted X-ray live-images.

According to a further aspect, also a medical imaging system for visualizing vascular structures is provided. The medical imaging system comprises an X-ray imaging device comprising an X-ray source and an X-ray detector, and a device for visualizing vascular structures according to one of the examples above. The X-ray imaging device is configured to provide at least a plurality of X-ray images of a region of interest of a patient as the second sequence of contrast X-ray images.

According to a further aspect, also a method for visualizing vascular structures is provided. The method comprises the following steps:

a1) providing a first sequence of non-contrast X-ray images of a region of interest of a patient for use as raw X-ray mask images;

a2) performing a first spatial subtraction for the first sequence of non-contrast X-ray images resulting in a first sequence of spatial-subtracted mask images;

b1) providing a second sequence of contrast X-ray images of the region of interest of a patient for use as raw X-ray live-images;

b2) performing a second spatial subtraction for the second sequence of contrast X-ray images resulting in a second sequence of spatial-subtracted X-ray live-images; and c) performing a temporal subtraction by subtracting the spatial-subtracted mask images from the spatial-subtracted X-ray live-images resulting in a sequence of spatial-temporal subtracted X-ray live-images.

According to an example, it is provided a step d) of displaying the sequence of spatial-temporal subtracted X-ray live-images.

According to an example, the first spatial subtraction and/or the second spatial subtraction comprises: estimating a soft tissue map of soft-tissue for each image of the sequence of X-ray images, and subtracting the estimated soft tissue map from the X-ray image.

According to an example, the estimating of the soft-tissue comprises harmonization techniques. Spatial low-frequencies are estimated in low multi-resolution pyramid levels, and un-wanted polarities or frequencies are attenuated or dumped.

According to an embodiment, it is proposed to reduce motion artifacts in abdominal DSA through a spatio-temporal approach. This performs a strong reduction of the amplitude of soft tissues in the spatial domain prior temporal subtraction that results in a reduction of motion artifacts after temporal subtraction. The proposed approach performs better than current methods used to compensate for motion artifacts after subtraction. The present approach overcomes the difficulty of motion estimation in transparent layers by a combination of spatial and temporal subtractions. This aims at correcting a combination of various motion sources and types.

It is proposed to prevent the occurrence of subtraction artifacts rather than correct for artifacts. In particular, two spatial subtractions are performed, one in the mask frames and one in the live frames, prior to a temporal subtraction of mask and live frames. As a result, the amplitude of motion artifacts is reduced.

In particular, use is made of a succession of two different types of subtractions, namely a spatial subtraction followed by a temporal subtraction. For the mask frame, a map of soft-tissue (mainly slowly varying) is estimated. The soft tissue map is subtracted from the mask frame (spatial subtraction) and the spatially subtracted mask is stored as SS-mask. For each live frame of the sequence, a map of soft-tissue is estimated. The soft tissue map is subtracted from the current live frame (spatial subtraction). The spatially subtracted live frame is stored as SS-live. Then, the temporal subtraction between SS-mask and SS-live is performed (temporal subtraction). A spatio-temporal subtracted STS-live output is obtained. The DSA output can then be displayed.

The invention may be used in all DSA imaging involving breathing or bowel gas motion, such as abdominal imaging for example.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION

Figure 1:
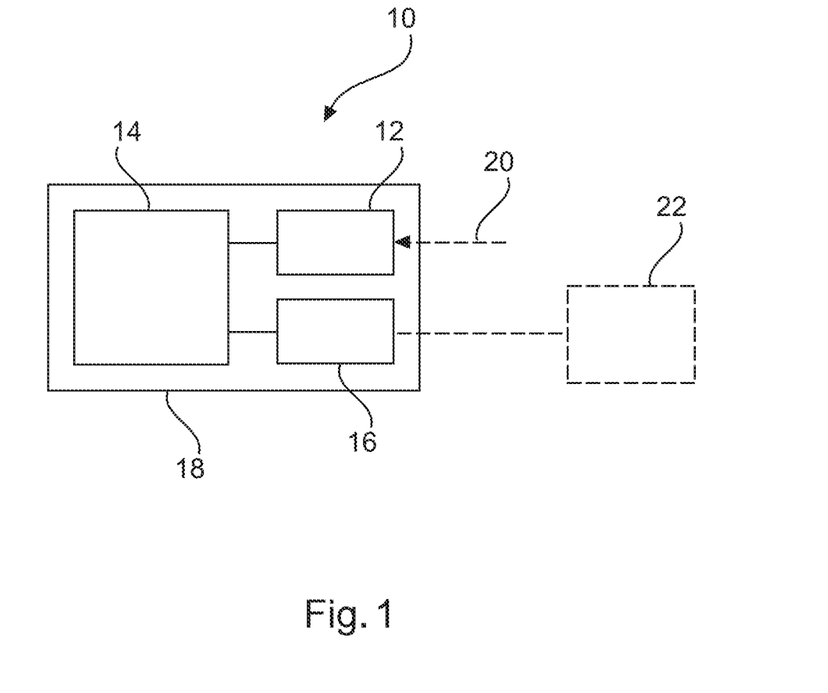
FIG. 1 shows a schematic setup of an example of a device for visualizing vascular structures.

FIG. 1 shows an example of a device 10 for visualizing vascular structures. The device 10 comprises a data provision processor 12, a data image processor 14, and an output interface 16.

The data provision processor 12 is configured to provide a first sequence of non-contrast X-ray images of a region of interest of a patient for use as raw X-ray mask images. The data provision processor 12 is also configured to provide a second sequence of contrast X-ray images of the region of interest of a patient for use as raw X-ray live-images.

The image processor 14 is configured to perform a first spatial subtraction for the first sequence of non-contrast X-ray images resulting in a first sequence of spatial-subtracted mask images. The image processor 14 is also configured to perform a second spatial subtraction for the second sequence of contrast X-ray images resulting in a second sequence of spatial-subtracted X-ray live-images. The image processor 14 is further configured to perform a temporal subtraction by subtracting the spatial-subtracted mask images from the spatial-subtracted X-ray live-images resulting in a sequence of spatial-temporal subtracted X-ray live-images.

The output interface 16 is configured to output the sequence of spatial-temporal subtracted X-ray live-images.

The data provision processor 12 is also referred to as provision unit or as data input interface. The image processor 14 is also referred to as data processing module. The output interface 16 is also referred to as data output unit or data output interface.

The term "unit" relates to a functional component or functional unit. The unit can be provided as an integrated part or module providing said function. The unit can also be provided as a separated unit, part or module.

As an example, the data provision processor 12, the data image processor 14, and the output interface 16 are provided integrated as indicated with frame 18.

The term "to output the sequence of spatial-temporal subtracted X-ray live-images" relates to providing the data of the sequence of the spatial-temporal subtracted X-ray live-images for further purposes. As an example, the data is used for displaying the respective sequence. As another example, the data is for further data processing steps such as comparison with pre-captured images and further live images, or a combination with pre-captured images and further live images.

As an option, indicated with hashed lines, a display 22 is provided, which is configured to display the sequence of spatial-temporal subtracted X-ray live-images.

The display receives the image data from the output interface. In an example, the display is provided as a main or subsidiary monitor in a medical imaging system.

Figure 2:
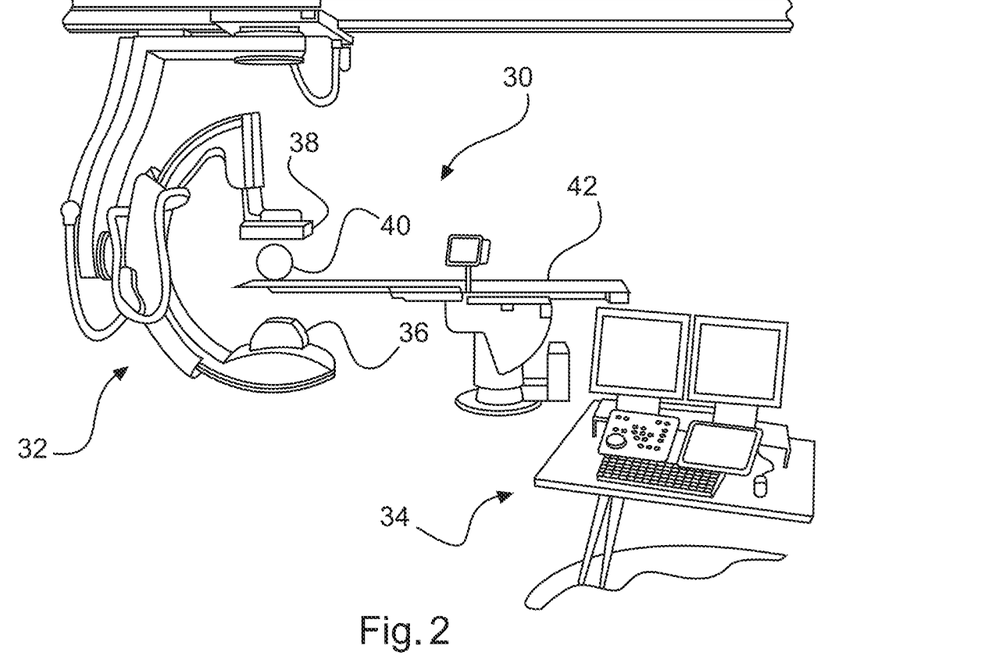
FIG. 2 shows an example of medical imaging system.

FIG. 2 shows an example of a medical imaging system 30 for visualizing vascular structures. The medical imaging system 30 comprises an X-ray imaging device 32 and a device 34 for visualizing vascular structures according to one of the above examples.

X-ray imaging device 32 comprises an X-ray source 36 and an X-ray detector 38 to image an object 40, for example a patient, arranged on a patient support 42. The X-ray imaging device 32 is shown as a C-arc system, but also other X-ray imaging devices are provided. The X-ray imaging device 32 is configured to provide at least a plurality of X-ray images of a region of interest of a patient as the second sequence of contrast X-ray images.

The X-ray imaging device provides the live X-ray image data of a patient.

In an example, the X-ray imaging device is also configured to provide a first sequence of non-contrast X-ray images of a region of interest of a patient.

Figure 3:
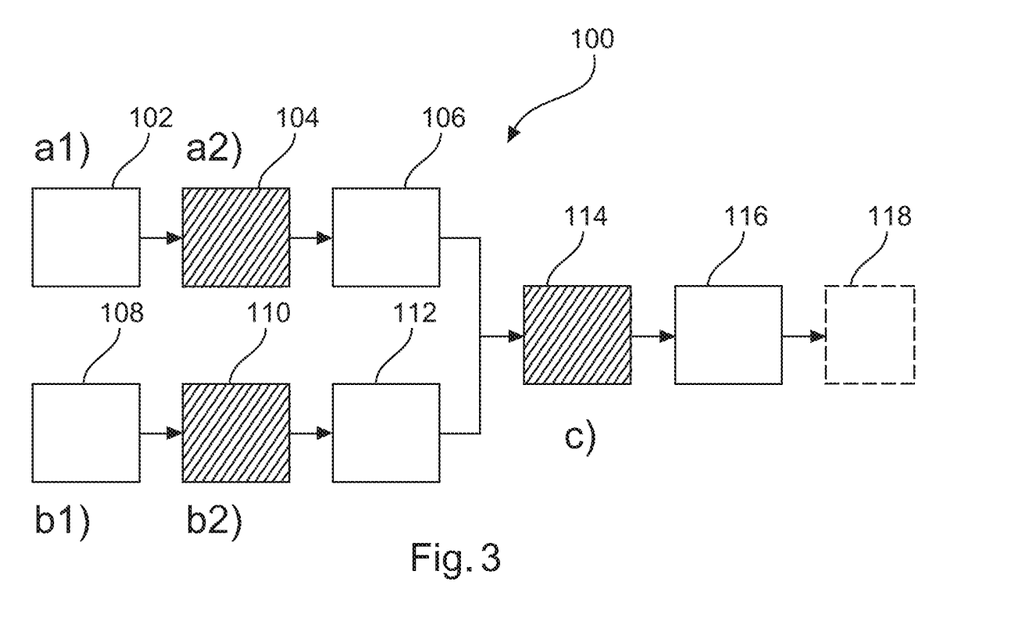
FIG. 3 shows an example of a method for visualizing vascular structures.

FIG. 3 shows an example of a method 100 for visualizing vascular structures, comprising the following steps:

In a first step 102, also referred to as step a1), a first sequence of non-contrast X-ray images of a region of interest of a patient is provided for use as raw X-ray mask images.

In a second step 104, also referred to as step a2), a first spatial subtraction is performed for the first sequence of non-contrast X-ray images resulting in a first sequence of spatial-subtracted mask images 106.

In a third step 108, also referred to as step b1), a second sequence of contrast X-ray images of the region of interest of a patient is provided for use as raw X-ray live-images.

In a fourth step 110, also referred to as step b2), a second spatial subtraction is performed for the second sequence of contrast X-ray images resulting in a second sequence of spatial-subtracted X-ray live-images 112.

In a fifth step 114, also referred to as step c), a temporal subtraction is performed by subtracting the spatial-subtracted mask images from the spatial-subtracted X-ray live-images resulting in a sequence 116 of spatial-temporal subtracted X-ray live-images.

The term "non-contrast X-ray images" relates to X-ray images of the region of interest without the application of any contrast enhancing substance, i.e. without injected or otherwise supplied contrast agent.

The term "contrast X-ray images" relates to X-ray images of the region of interest with applied contrast enhancing substances, e.g. with injected or otherwise supplied contrast agent. The contrast agent may be provided into the bloodstream or blood flow in the vessels and thus enhances the visibility of the vasculature structure.

In an example, the first spatial subtraction is performed for each image of the first sequence of non-contrast X-ray images.

In an example, the second spatial subtraction is performed for each image of the second sequence of contrast X-ray images.

The raw mask images are pre-processed e.g. by subtracting soft-tissue, before the temporal subtraction takes place.

The same approach is also provided for the live images. In other words, the live images are also pre-processed before the temporal subtraction takes place.

Both pre-processing sub-steps must be done before the temporal subtraction.

The "raw X-ray mask images" can also be referred to as raw mask images, or basic X-ray mask data or basic mask data or X-ray mask basics or mask basics.

The "raw X-ray live-images" can also be referred to as raw live-images, or basic X-ray live-data or live-data or X-ray live-basics.

The "spatial-temporal subtracted X-ray live-images" can also be referred to as vessel-enhanced X-ray live-images or enhanced X-ray live-data or enhanced live-images or enhanced live-data.

The images of the first and second sequence are also referred to as frames, e.g. first frames and second frames.

By providing two spatial subtractions in both the mask and the live frames, prior to temporal subtraction, i.e. before the mask image is subtracted from the live image, the occurrence of subtraction artifacts is prevented or at least reduced. The need for correcting for artifacts after the subtraction is thus reduced. The two spatial subtractions in both the mask and the live frames reduce the amplitude of motion artifacts in the subtraction result.

The subtractions in steps a2) and b2) are referred to as spatial subtractions, because here content within the spatial domain of the image is used for the subtraction.

The subtraction in step c) is referred to as a temporal subtraction, because here images of different sequences acquired at different points in time, i.e. images of different points on the time domain, are used for the subtraction. The live image is used and by subtracting the previous image, the difference remains, i.e. those parts of the image where contrast agent is present in the image. Hence, a better visualization of the vasculature is provided. Briefly said, the subtraction reduces the resulting image to the differing parts. Tissue related content that is not subject to contrast injection is eliminated.

However, motion between the two images (i.e. the two sequences) may result in artifacts. Part of this can be compensated by identifying different states of a motion cycle and by assigning images of the first sequence to respective matching images of matching motion states of the second sequence.

In an example, the steps a1) and a2) are performed prior to acquiring the second sequence of images.

In another example, the steps a1) and a2) are performed parallel to the steps b1) and b2).

The images that form the basis for step a1) are nevertheless acquired at a different, i.e. earlier, point in time than the acquisition of the second sequence of images.

In an example, a spatio-temporal image subtraction for abdominal DSA is provided.

As an example, in interventional X-ray, digital subtract angiography (DSA) may be performed to visualize vascular structures. The images are obtained by subtracting a non-injected mask frame from injected frames. In case of motion, and in particular breathing or bowel gas motion, the quality of subtracted images may be strongly reduced and the resulting artifacts frequently reduce the diagnostic value of the images.

X-ray images are transparency images and observed motion may result from the super-imposition of various motion layers with different characteristics. Further accurate compensation is provided for all the sources of motion with the present approach.

In an example, the spatio-temporal approach is combined with a selection of an optimal frame in the mask sub-sequence to further improve STS-live images.

In an example, it is provided to apply rigid motion compensation between mask and live frames.

In an example, the current temporal subtraction is swapped by a motion-compensated temporal subtraction.

In an example, motion artifacts are reduced in abdominal DSA through a spatio-temporal approach. The method performs a strong reduction of the amplitude of soft tissues in the spatial domain prior temporal subtraction that results in a reduction of motion artifacts after temporal subtraction. The proposed approach shows an improved performance than current methods used to compensate for motion artifacts after subtraction.

In an example, temporal subtraction is a motion compensated subtraction, which is a subtraction of the spatial-subtracted motion compensated mask images from the spatial-subtracted X-ray live-images.

As an option, indicated in FIG. 3 with hashed lines, it is provided a further step 118, also referred to as step d), in which the sequence of spatial-temporal subtracted X-ray live-images are displayed.

In an example, not further shown, the first spatial subtraction and/or the second spatial subtraction comprises: estimating a soft tissue map of soft-tissue for each image of the sequence of X-ray images, and subtracting the estimated soft tissue map from the X-ray image.

The subtraction of the soft-tissue reduces the range of amplitudes within the image.

In an example, for the mask frame, a map of soft-tissue (mainly spatially slowly varying) is estimated. Further, the soft tissue map is subtracted from the mask frame (which is referred to as the spatial subtraction). The spatially subtracted image(s) is (are) stored as a spatially subtracted mask.

In an example, for each live frame, a map of soft-tissue is estimated. The soft tissue map is subtracted from the current live frame (which is referred to as the spatial subtraction). The spatially subtracted frame(s) is (are) stored as a spatially subtracted live images.

In an example, the temporal subtraction is performed between the spatial subtraction mask and the spatial subtraction live data (which is referred to as the temporal subtraction).

In an example, a spatio-temporal (or spatial-temporal) subtracted live output is obtained as a result, or output, of a digital subtraction angiography (DSA).

In an option, the output of the digital subtraction angiography is displayed.

The estimation of a soft-tissue map can be done by so-called harmonization techniques. Spatial low-frequencies can be estimated in low multi-resolution pyramid levels, and the resulting estimation further processed to damp un-wanted polarities or frequencies (vessels show a known contrast polarity, and their maximum size is known).

In an example, not further shown, the estimating of the soft-tissue comprises harmonization techniques. Spatial low-frequencies are estimated in low multi-resolution pyramid levels, and un-wanted polarities or frequencies are attenuated or dumped. For example, vessels show a known contrast polarity, and their maximum size is known. This allows to flatten the image.

Figure 4:
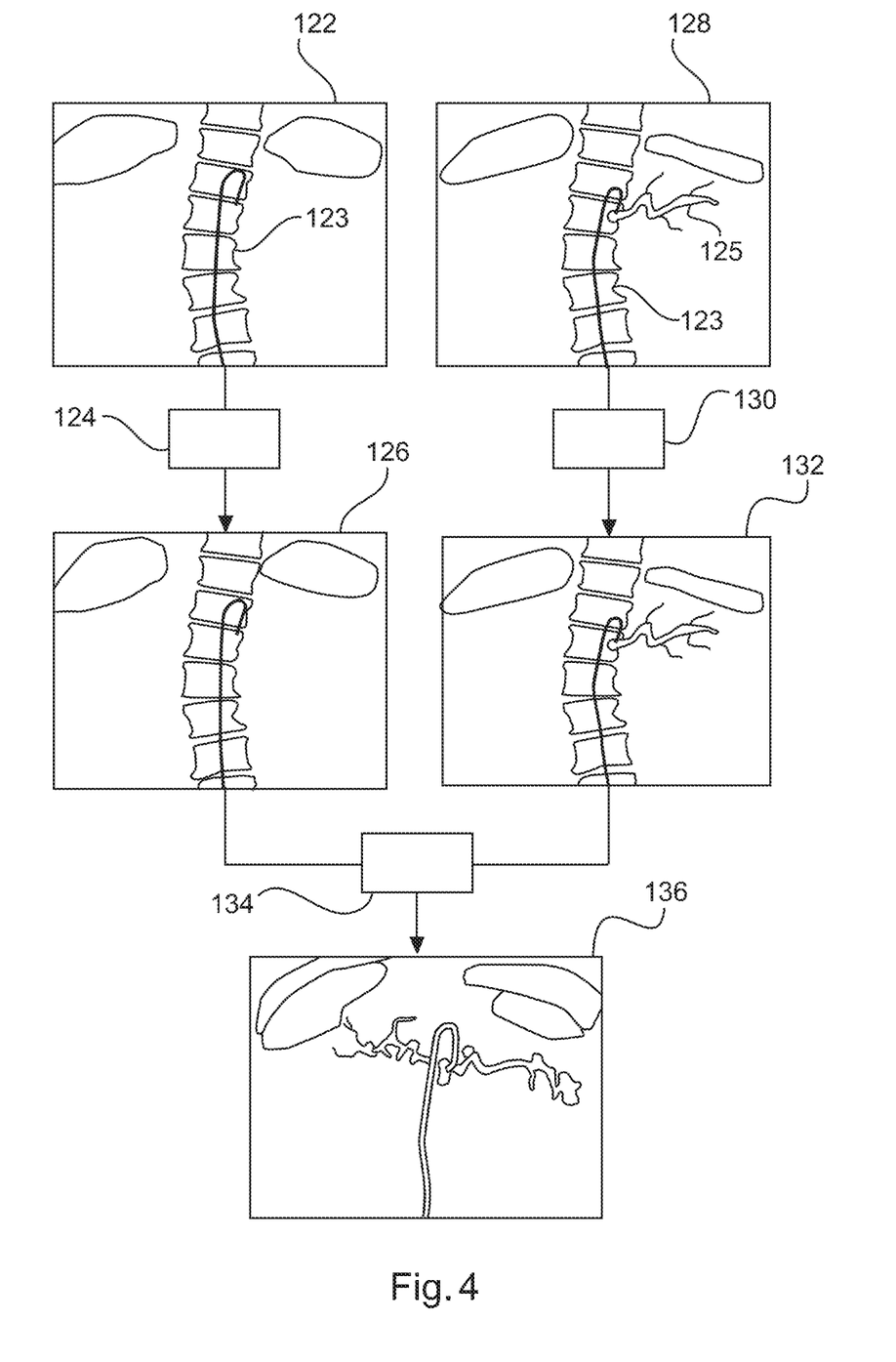
FIG. 4 shows examples for images used for the method of FIG. 3.

FIG. 4 shows a further example of the image processing.

In the left column, a mask image 112 is provided showing a region of interest of a patient, e.g. a vertebra structure 123. After a spatial subtraction step 124, a spatial subtracted mask image 126 is provided.

In the right column, a live input image 128 is provided showing the region of interest of a patient, e.g. a vertebra structure, but also with contrast injected vessels 125. After a spatial subtraction step 130, a spatial subtracted live image 132 is provided.

Following, a temporal subtraction 134 is provided resulting in an output live image 136 showing the vasculature structure in an improved way.

Figure 5:
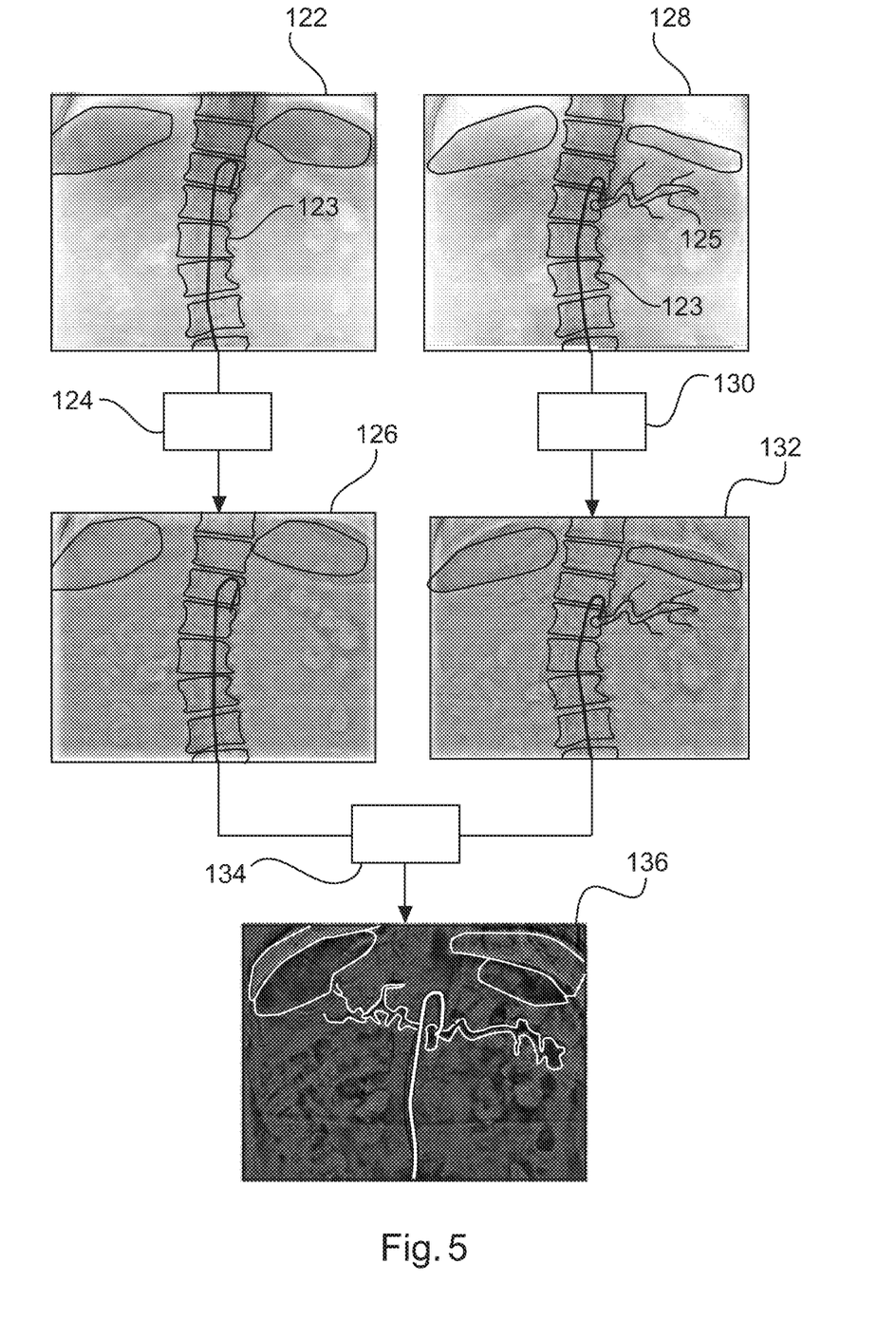
FIG. 5 shows the examples of FIG. 4 as photographic images.

FIG. 4 shows the images with lines only. FIG. 5 shows the images of FIG. 4 in a photographic manner.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section. A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A vascular structure visualization apparatus, comprising:
   a data provision processor configured to provide a set of non-contrast X-ray images of a region of interest of a patient and to provide a set of contrast X-ray images of the region of interest of a patient;
   an image processor configured to perform spatial subtraction of the non-contrast X-ray images to generate spatially-subtracted mask images, and to perform spatial subtraction of the contrast X-ray images to generate spatially-subtracted X-ray live-images, wherein the image processor is further configured to perform a temporal subtraction by subtracting the spatially-subtracted mask images from the spatially-subtracted X-ray live-images to generate spatial-temporal subtracted X-ray live-images; and
   an output interface configured to output the spatial-temporal subtracted X-ray live-images.

2. The vascular structure visualization apparatus according to claim 1, further comprising a display configured to display the spatial-temporal subtracted X-ray live-images.

3. The vascular structure visualization apparatus according to claim 1, wherein the image processor is configured to perform the temporal subtraction by performing motion-compensation.

4. The vascular structure visualization apparatus according to claim 3, wherein the motion-compensated subtraction comprises subtraction of the spatial-subtracted mask images from the spatial-subtracted X-ray live-images.

5. The vascular structure visualization apparatus according to claim 1, wherein the spatial-subtracted mask images correspond to an estimation of a soft-tissue map.

6. The vascular structure visualization apparatus according to claim 1, wherein the image processor is configured to estimate a soft tissue map indicating soft tissue in each image of the non-contrast X-ray images and to subtract the estimated soft tissue map from the non-contrast X-ray images to generate the spatially-subtracted mask images.

7. The vascular structure visualization apparatus according to claim 6, wherein the image processor is configured to estimate the soft tissue map utilizing harmonization, and wherein harmonization comprises estimating spatial low-frequencies in low multi-resolution pyramid levels and attenuating or discarding un-wanted polarities or frequencies.

8. A medical imaging system for visualizing vascular structures, comprising:
   an X-ray imaging device comprising an X-ray source and an X-ray detector; and
   a vascular structure visualization device comprising an image processor configured to perform spatial subtraction of non-contrast X-ray images to generate spatial-subtracted mask images, and to perform spatial subtraction of contrast X-ray images to generate spatial-subtracted X-ray live-images, wherein the image processor is further configured to perform a temporal subtraction by subtracting the spatial-subtracted mask images from the spatial-subtracted X-ray live-images to generate spatial-temporal subtracted X-ray live-images.

9. The medical imaging system according to claim 8, wherein the X-ray imaging device is configured to provide at least a plurality of X-ray images of a region of interest of a patient as the contrast X-ray images.

10. The medical imaging system according to claim 8, wherein the image processor is configured to perform the temporal subtraction by performing motion-compensation.

11. The medical imaging system according to claim 8, wherein the motion-compensated subtraction comprises subtraction of the spatial-subtracted mask images from the spatial-subtracted X-ray live-images.

12. The medical imaging system according to claim 8, wherein the spatial-subtracted mask images correspond to an estimation of a soft-tissue map.

13. A method for visualizing vascular structures, comprising:
   providing a first set of non-contrast X-ray images of a region of interest of a patient;
   performing spatial subtraction for the first set of non-contrast X-ray images resulting in a first set of spatial-subtracted mask images;
   providing a set of contrast X-ray images of the region of interest of a patient;
   performing spatial subtraction for the set of contrast X-ray images resulting in a set of spatial-subtracted X-ray live-images; and
   performing a temporal subtraction by subtracting the first set of spatial-subtracted mask images from the set of spatial-subtracted X-ray live-images resulting in a sequence of spatial-temporal subtracted X-ray live-images.

14. The method according to claim 13, wherein the temporal subtraction is a motion-compensated subtraction which comprises subtraction of a set of spatial-subtracted motion-compensated mask images from the set of spatial-subtracted X-ray live-images.

15. The method according to claim 13, wherein spatial subtraction comprises:
   estimating a soft tissue map of soft-tissue for each X-ray image; and
   subtracting the estimated soft tissue map from the corresponding X-ray image.

16. The method according to claim 15, wherein estimating of the soft-tissue map comprises performing harmonization, and wherein harmonization comprises estimating spatial low-frequencies in low multi-resolution pyramid levels and attenuating or discarding un-wanted polarities or frequencies.

17. A non-transitory computer-readable medium having stored thereon instructions that when executed by processing circuitry of a vascular visualization device causes the processing circuitry to:
   provide a set of non-contrast X-ray images of a region of interest of a patient;
   perform spatial subtraction for the set of non-contrast X-ray images resulting in a set of spatial-subtracted mask images;
   provide a set of contrast X-ray images of the region of interest of a patient;
   perform spatial subtraction for the set of contrast X-ray images resulting in a set of spatial-subtracted X-ray live-images; and
   perform a temporal subtraction by subtracting the set of spatial-subtracted mask images from the set of spatial-subtracted X-ray live-images resulting in a sequence of spatial-temporal subtracted X-ray live-images.

18. The non-transitory computer-readable medium according to claim 17, wherein the temporal subtraction is a motion-compensated subtraction which comprises subtraction of a set of spatial-subtracted motion-compensated mask images from the set of spatial-subtracted X-ray live-images.

19. The non-transitory computer-readable medium according to claim 17, wherein spatial subtraction comprises:
   estimating a soft tissue map of soft-tissue for each X-ray image; and
   subtracting the estimated soft tissue map from the corresponding X-ray image.

20. The non-transitory computer-readable medium according to claim 19, wherein estimating of the soft-tissue map comprises performing harmonization, and wherein harmonization comprises estimating spatial low-frequencies in low multi-resolution pyramid levels and attenuating or discarding un-wanted polarities or frequencies.

* * * * *